(12) United States Patent
Kitamura et al.

(10) Patent No.: US 9,492,094 B2
(45) Date of Patent: Nov. 15, 2016

(54) BLOOD PRESSURE MONITOR

(75) Inventors: Masashi Kitamura, Muko (JP); Kai Zhong, Dalian (CN); Chun-Peng Zhang, Dalian (CN)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 879 days.

(21) Appl. No.: 13/361,320

(22) Filed: Jan. 30, 2012

(65) Prior Publication Data

US 2012/0130259 A1    May 24, 2012

Related U.S. Application Data

(63) Continuation of application No. PCT/JP2010/062431, filed on Jul. 23, 2010.

(30) Foreign Application Priority Data

Jul. 31, 2009    (JP) ................................. 2009-179586

(51) Int. Cl.
*A61B 5/02* (2006.01)
*A61B 5/022* (2006.01)
*A61B 5/021* (2006.01)

(52) U.S. Cl.
CPC ........... *A61B 5/022* (2013.01); *A61B 5/02141* (2013.01); *A61B 2560/0425* (2013.01)

(58) Field of Classification Search
CPC ........................... A61B 5/022; A61B 5/02141
USPC .................................................. 600/490–499
See application file for complete search history.

(56) References Cited

U.S. PATENT DOCUMENTS

| | | | | |
|---|---|---|---|---|
| 4,706,684 A | * | 11/1987 | Sorensen et al. | ............. 600/490 |
| 6,344,025 B1 | | 2/2002 | Inagaki et al. | |
| 2007/0038133 A1 | * | 2/2007 | Kishimoto | ............. A61B 5/022 600/490 |
| 2007/0197923 A1 | | 8/2007 | Kishimoto et al. | |

FOREIGN PATENT DOCUMENTS

| | | | | |
|---|---|---|---|---|
| JP | 57-145640 A | | 9/1982 | |
| JP | 60-073503 U | | 5/1985 | |
| JP | 2004-81743 | * | 3/2004 | ............. A61B 5/022 |
| JP | 2004-081743 A | | 3/2004 | |
| JP | 2007-185367 A | | 7/2007 | |
| KR | 20000012656 A | | 3/2000 | |

OTHER PUBLICATIONS

International Search Report issued in PCT/JP2010/062431 mailed on Aug. 17, 2010 with English translation thereof, 4 pages.
Office Action issued in corresponding Russian Application No. 2012107493/14(011303) dated Jun. 26, 2014, and English translation thereof (7 pages).

* cited by examiner

*Primary Examiner* — Tiffany Weston
(74) *Attorney, Agent, or Firm* — Osha Liang LLP

(57) ABSTRACT

In a blood pressure monitor, when a main unit is mounted on a mounting surface such as a desk, a bulging region of a first tube and a bulging region of a second tube, both located at a rear surface of the main unit, come into contact with the mounting surface. This can avoid the main unit from sliding even when the main unit is pulled by the first and second tubes. Consequently, a blood pressure monitor has a configuration in which the main unit is less likely to slide over the mounting surface even when the main unit is pulled by tubes connected to the main unit.

5 Claims, 7 Drawing Sheets

BLOOD PRESSURE MONITOR

This is a continuation of application Serial No. PCT/JP2010/062431 filed Jul. 23, 2010, the contents of which are incorporated herein by reference.

BACKGROUND OF THE INVENTION

1. Field of the Invention

The present invention relates to a blood pressure monitor.

2. Description of the Background Art

Japanese Patent Laying-Open No. 57-145640 (Patent Document 1) discloses a manual pressurizing blood pressure monitor. The manual pressurizing blood pressure monitor includes a main unit, a rubber ball serving as a manual pressurizing device connected to this main unit with a tube, and a cuff connected to the main unit with the tube.

With size reduction of built-in electronic devices, the main unit has been reduced in weight year by year. Therefore, during blood pressure measurement using this manual pressurizing blood pressure monitor, the main unit mounted on a mounting surface such as a desk is likely to slide over the mounting surface by being pulled by the tube connected to the main unit.

Sliding of the main unit degrades the usability of the manual pressurizing blood pressure monitor, and also imparts undesirable vibrations to a sensor and the like built into the main unit, which may affect the accuracy in blood pressure measurement. A rubber protrusion for preventing sliding may be provided on the rear surface of the main unit. However, providing such a rubber protrusion increases the manufacturing cost of the manual pressurizing blood pressure monitor.

An automatic pressurizing blood pressure monitor with a pressurizing mechanism built into the main unit is also provided with a tube between the main unit and the cuff. Therefore, during blood pressure measurement, the main unit mounted on a mounting surface such as a desk is likely to slide over the mounting surface by being pulled by the tube connected to the main unit.

Accordingly, during use of a blood pressure monitor, a main unit is likely to slide over a mounting surface by being pulled by a tube connected to the main unit.

SUMMARY OF INVENTION

One or more embodiments of the present invention provide a blood pressure monitor having a configuration in which a main unit is less likely to slide over a mounting surface even when the main unit is pulled by a tube connected to the main unit.

One or more embodiments of the present invention are directed to a blood pressure monitor including a main unit to be mounted on a mounting surface and having a front surface and a rear surface, a manual pressurizing mechanism, a cuff to be wound around a subject's predetermined body section, a first tube connecting the main unit and the manual pressurizing mechanism, and a second tube connecting the main unit and the cuff. At least one of the first tube and the second tube is arranged fixedly at the rear surface of the main unit so as to partially come into contact with the mounting surface.

One or more embodiments of the present invention are directed to a blood pressure monitor including a main unit to be mounted on a mounting surface and having a front surface and a rear surface, a cuff to be wound around a subject's predetermined body section, and a tube connecting the main unit and the cuff. The tube is arranged fixedly at the rear surface of the main unit so as to partially come into contact with the mounting surface.

One or more embodiments of the present invention can provide a blood pressure monitor having the configuration in which the main unit is less likely to slide over the mounting surface even when the main unit is pulled by the tube connected to the main unit.

The foregoing and other embodiments of the present invention will become more apparent from the following detailed description of the present invention when taken in conjunction with the accompanying drawings.

DETAILED DESCRIPTION OF INVENTION

Figure 1:
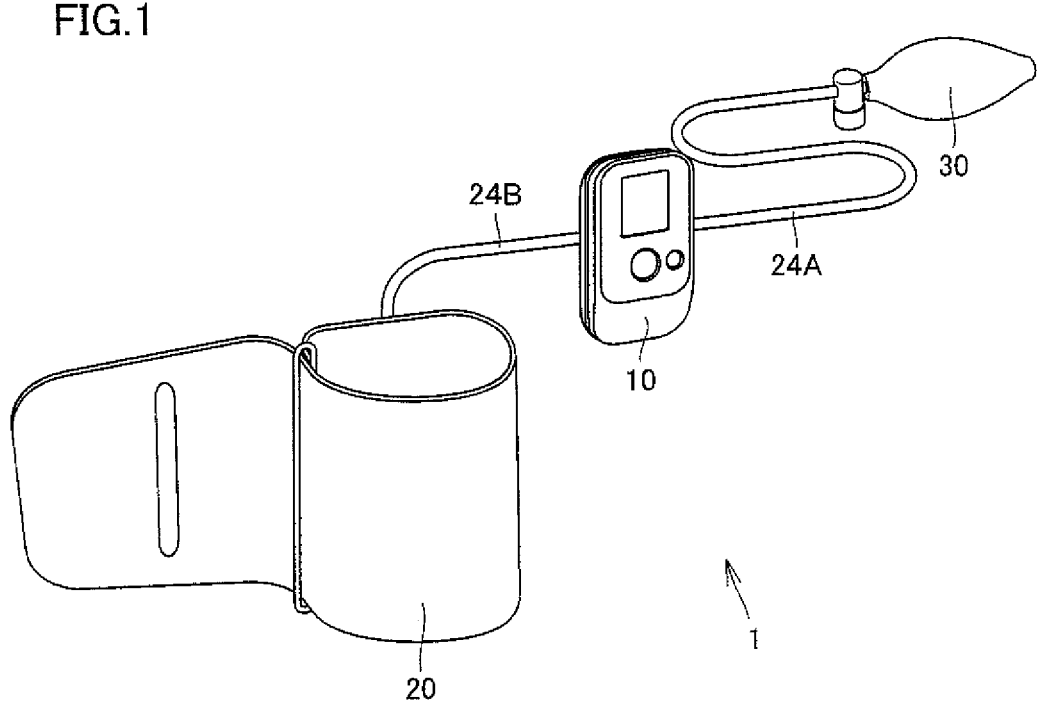
FIG. 1 shows an overall configuration of a blood pressure monitor according to a first embodiment.

Hereinafter, a blood pressure monitor according to one or more embodiments of the present invention implemented by applying one or more embodiments of the present invention to a manual pressurizing blood pressure monitor, by way of example, will be described with reference to the drawings. In the respective embodiments which will be described below, any reference to the number, amount and the like is not always intended to limit the scope of the present invention to such number, amount and the like, unless otherwise specified. If there are a plurality of embodiments below, it has originally been expected that the configuration of each of such embodiments may be combined appropriately, unless otherwise specified.

First Embodiment

With reference to FIGS. 1 to 7, a manual pressurizing blood pressure monitor 1 according to a first embodiment will be described. First, with reference to FIGS. 1 and 3 to 6, an external configuration of manual pressurizing blood pressure monitor 1 will be described.

External Configuration of Manual Pressurizing Blood Pressure Monitor 1

Manual pressurizing blood pressure monitor 1 according to the present embodiment includes a flat-shaped main unit 10, a cuff 20 to be wound around a subject's predetermined body section such as an upper arm, and a rubber ball 30, for example, as a manual pressurizing mechanism.

Rubber ball 30 is connected to main unit 10 with a first tube 24A. Cuff 20 is connected to main unit 10 with a second tube 24B. Rubber ball 30 is compressed by a subject to feed air into an air bag of cuff 20 through first tube 24A and second tube 24B. A housing constituting main unit 10 is implemented by molded resin, molded sheet metal or the like. First tube 24A and second tube 24B are implemented by polyvinyl chloride, natural rubber, silicone rubber, elastomer, or the like.

A display unit 40 for displaying measurement results and the like, an operating unit 41 for accepting a subject's instruction input, and the like are provided at a front surface 10A of main unit 10. For example, operating unit 41 has the functions such as a power switch for switching on/off of power supply, a measuring switch for inputting an instruction to start measurement, and a memory switch for inputting an instruction to read and display past measurement results. Display unit 40 is implemented by, for example, a display of liquid crystal or the like.

A projecting portion 12 extending laterally as viewed in the drawing is provided at the rear surface of main unit 10 in a position closer to the upper region than to the central region of main unit 10. Recessed portions 12a depressed toward the front surface of main unit 10 are provided on both sides of this projecting portion 12. Plugs 11A and 11B are provided to extend laterally from the side surfaces of projecting portion 12 so as to be enclosed in recessed portions 12a, respectively. A battery cover 15 is provided on the rear surface of main unit 10 in a position closer to the lower region than to the central region of main unit 10.

It is to be noted that the shape of main unit 10 of manual pressurizing blood pressure monitor 1 is not limited to such an example. Provision of rubber ball 30 as a manual pressurizing mechanism is not a limitative example. Fluid for pressurizing cuff 20 is not limited to air.

Hardware Configuration

Figure 2:
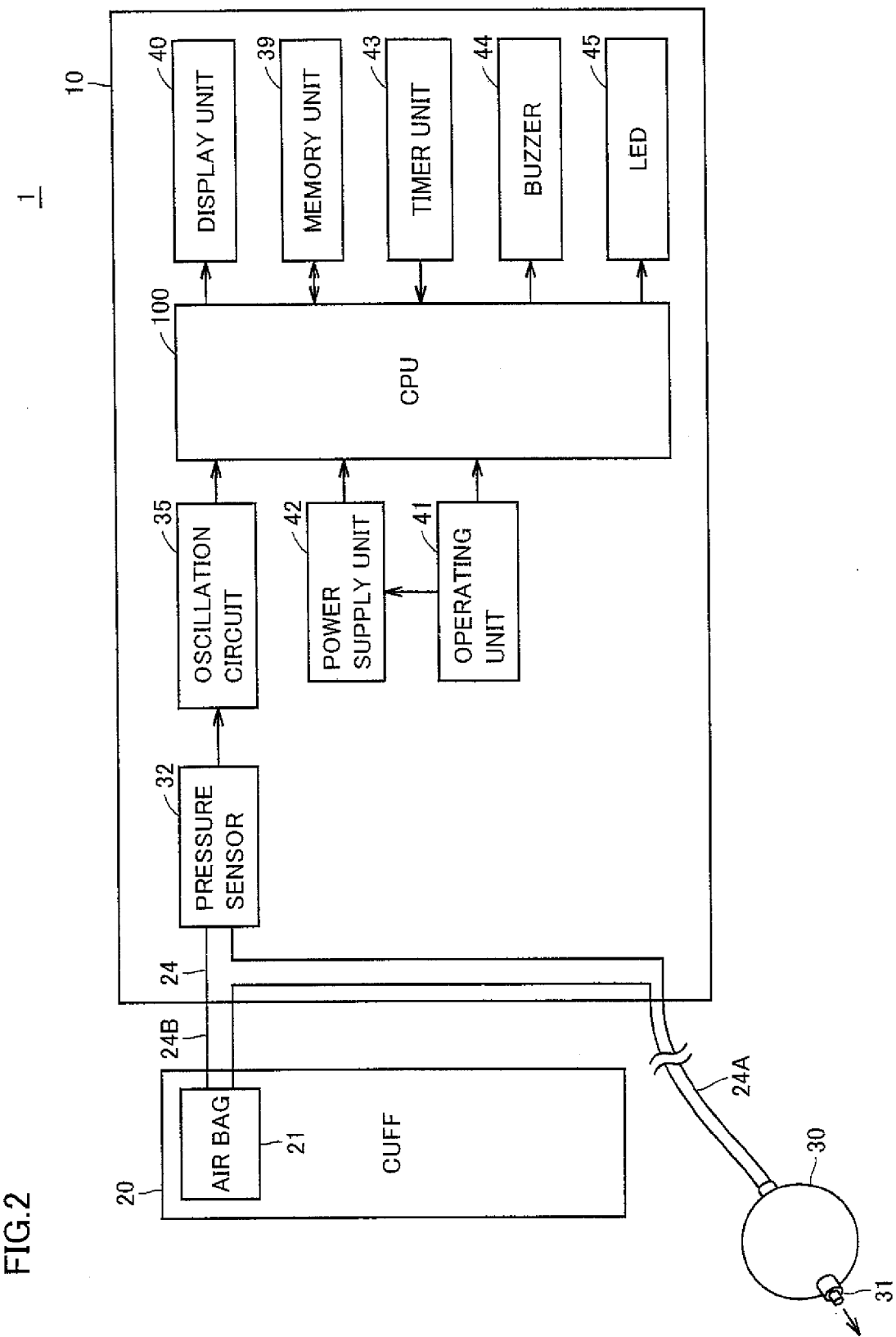
FIG. 2 is a block diagram showing a hardware configuration of the blood pressure monitor according to the first embodiment.
Figure 3:
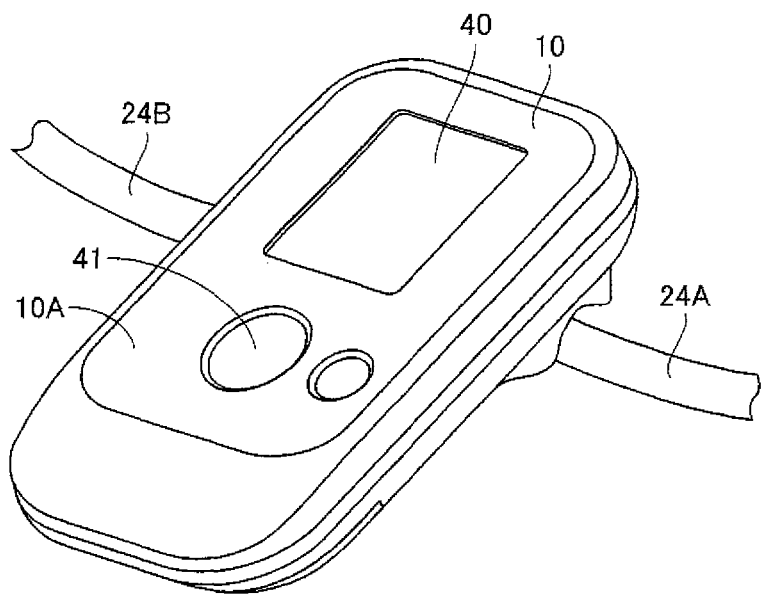
FIG. 3 is a perspective view showing a front side (front surface) of a main unit of the blood pressure monitor according to the first embodiment.
Figure 4:
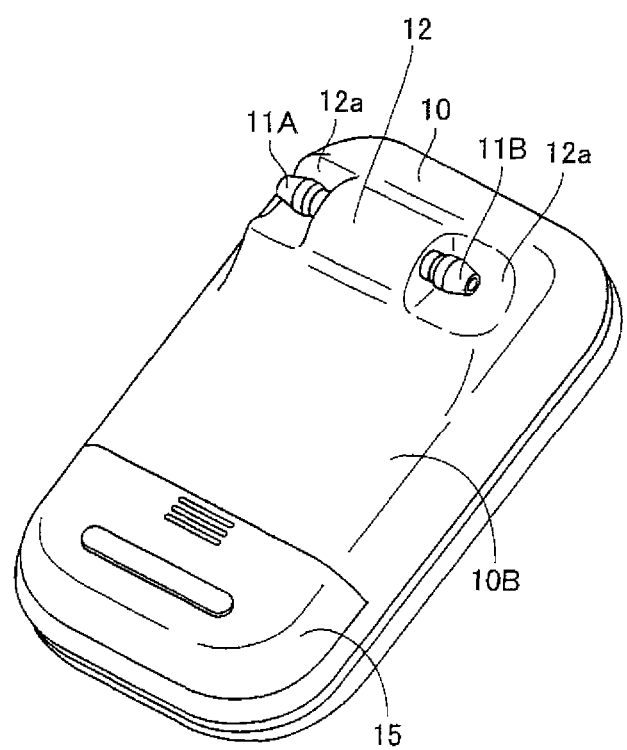
FIG. 4 is a perspective view showing a back side (rear surface) of the main unit of the blood pressure monitor according to the first embodiment with tubes disconnected therefrom.
Figure 5:
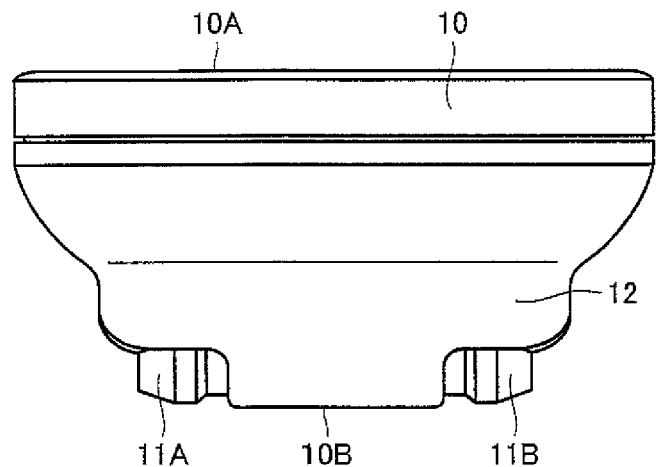
FIG. 5 is a plan view (top portion) of the main unit of the blood pressure monitor according to the first embodiment with tubes disconnected therefrom.
Figure 6:
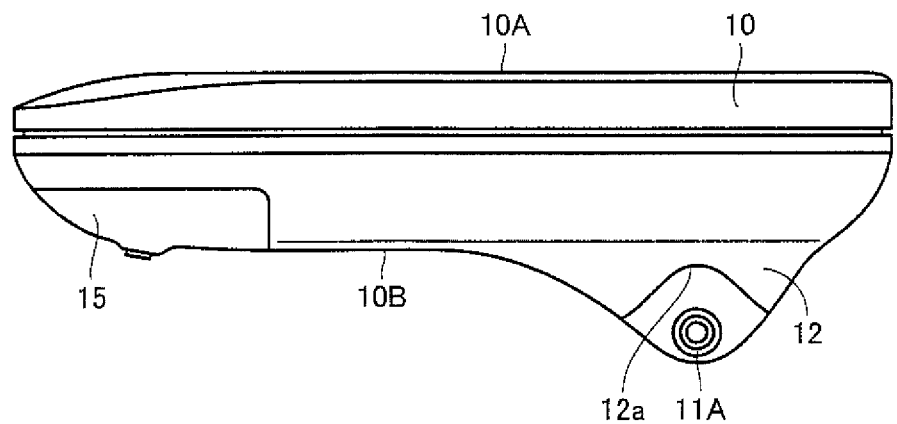
FIG. 6 shows a side surface (right side) of the main unit of the blood pressure monitor according to the first embodiment with tubes disconnected therefrom.

With reference to FIG. 2, a hardware configuration of manual pressurizing blood pressure monitor 1 according to the present embodiment will now be described. Cuff 20 of manual pressurizing blood pressure monitor 1 includes an air bag 21 containing air. Rubber ball 30 supplies/exhausts air to/from air bag 21 through first tube 24A and second tube 24B.

A minute exhaust hole 31 through which air is exhausted at a constant speed is arranged in a predetermined position of rubber ball 30. Pressing a dedicated switch (not shown) included in operating unit 41 allows rubber ball 30 to rapidly exhaust air. The subject can supply air to air bag 21 by compressing rubber ball 30.

Main unit 10 includes a CPU (Central Processing Unit) 100 for intensively controlling and monitoring each unit, a pressure sensor 32, an oscillation circuit 35, a nonvolatile memory unit 39, display unit 40, operating unit 41, a power supply unit 42, a timer unit 43 for carrying out a timing operation, a buzzer 44 for producing an alarm or a beep, and an LED (Light Emitting Diode) 45 for emitting light.

Pressure sensor 32 is a device for sensing a cuff pressure signal indicating a pressure in air bag 21 (hereinafter referred to as "cuff pressure"). Pressure sensor 32 varies in capacity value depending on the sensed pressure. Oscillation circuit 35 outputs a signal having an oscillation frequency in accordance with the capacity value of pressure sensor 32, to CPU 100. CPU 100 converts the signal received from oscillation circuit 35 to a pressure, to thereby sense the pressure (cuff pressure).

Memory unit 39 stores programs causing CPU 100 to execute predetermined operations and various types of information such as measurement result information. Power supply unit 42 supplies electric power to CPU 100 in accordance with a power-on instruction from operating unit 41.

Coupling Mechanism Among Plugs and Tubes

Figure 7:
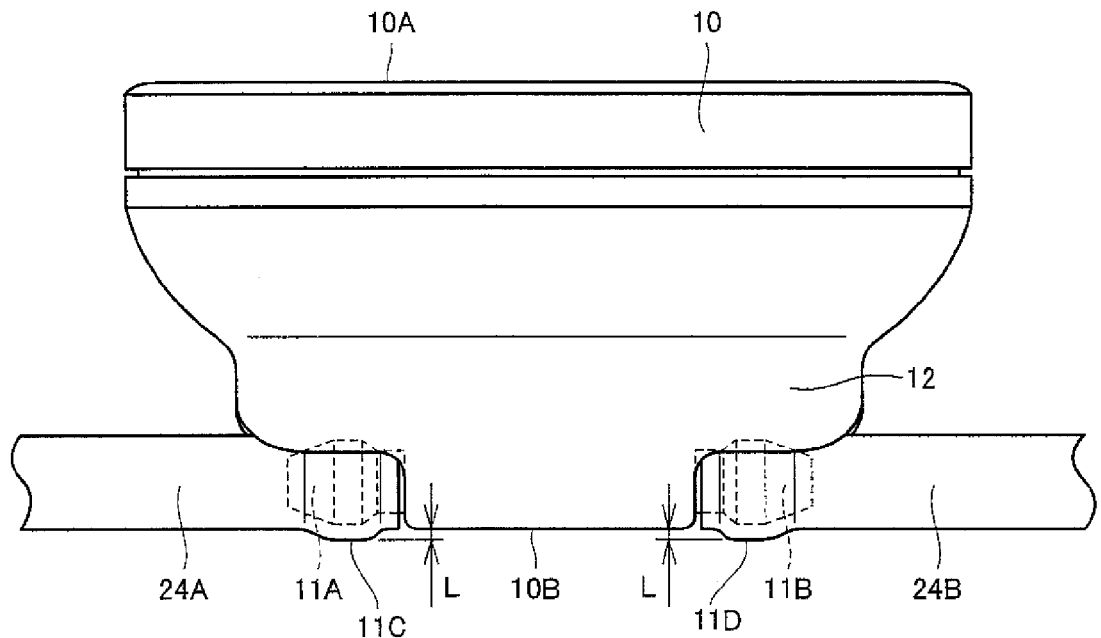
FIG. 7 is a plan view (top portion) of the main unit of the blood pressure monitor according to the first embodiment with tubes connected thereto.

With reference to FIG. 7, a coupling mechanism among first plug 11A, second plug 11B, first tube 24A, and second tube 24B will now be described in detail. In the present embodiment, first plug 11A arranged to project toward one side surface and second plug 11B arranged to project toward the other side surface are provided in projecting portion 12.

First plug 11A is attached to one side surface of projecting portion 12 such that, when first tube 24A is fitted fixedly over first plug 11A, a region 11C pressed from the inner side by a bulge provided for first plug HA to bulge outwardly relative to the remaining surface region at the front side of first tube 24A is located in a position projecting downwardly relative to the bottom end of projecting portion 12 (by a distance L: about 0.5 mm). Accordingly, when main unit 10 is mounted on the mounting surface, the surface of region 11C of first tube 24A bulging outwardly comes into contact with the mounting surface.

Similarly, second plug 11B is attached to the other side surface of projecting portion 12 such that, when second tube 24B is fitted fixedly over second plug 11B, a region 11D pressed from the inner side by a bulge provided for second plug 11B to bulge outwardly relative to the remaining surface region at the front side of second tube 24B is located in a position projecting downwardly relative to the bottom end of projecting portion 12 (by a distance L: about 05 mm). Accordingly, when main unit 10 is mounted on the mounting surface, the surface of region 11D of second tube 24B bulging outwardly comes into contact with the mounting surface.

Through use of this configuration, when main unit 10 is mounted on the mounting surface such as a desk, bulging region 11C of first tube 24A and bulging region 11D of second tube 24B, both located at rear surface 10B of main unit 10, come into contact with the mounting surface. Because first tube 24A and second tube 24B are implemented by polyvinyl chloride, natural rubber, silicone rubber, elastomer, or the like having a coefficient of friction greater than that of the surface of main unit 10, sliding of main unit 10 can be avoided even when main unit 10 is pulled by first tube 24A and second tube 24B.

Even when main unit 10 is pulled by first tube 24A and second tube 24B, main unit 10 can also be prevented from rotating because sliding of main unit 10 is avoided.

As described above, because outwardly bulging regions 11C and 11D of first tube 24A and second tube 24B, respectively, connected to main unit 10 come into contact with the mounting surface, main unit 10 is less likely to slide over the mounting surface even when main unit 10 is pulled. As a result, undesirable vibrations are not imparted to pressure sensor 32 and the like built into main unit 10, which can achieve improved accuracy in blood pressure measurement. In addition, the unnecessity to provide another member for preventing main unit 10 from sliding avoids an increase in the manufacturing cost of the manual pressurizing blood pressure monitor.

Figure 8:
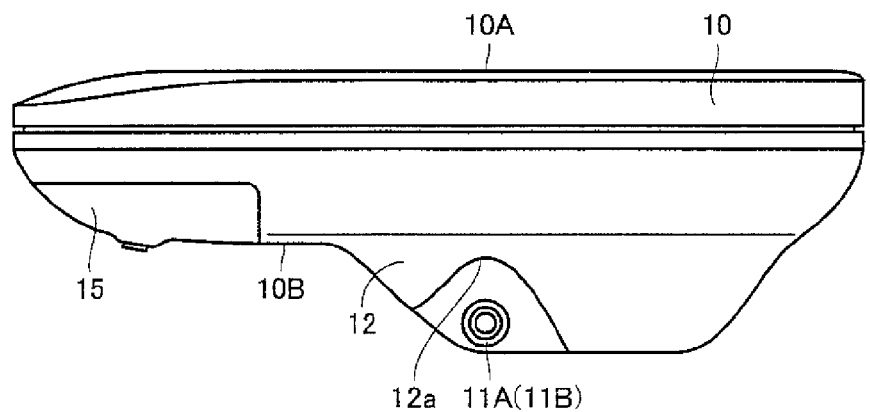
FIG. 8 shows a side surface (right side) of a main unit of a blood pressure monitor according to another mode of the first embodiment with tubes disconnected therefrom.

The above-described embodiment illustrates the configuration in which first plug 11A and second plug 11B are arranged at rear surface 10B in the position closer to the upper region than to the central region of main unit 10, however, this configuration is not a limitative example. As shown in the side view of FIG. 8, for example, first plug 11A and second plug 11B may be arranged at rear surface 10B in the central region of main unit 10.

First plug 11A and second plug 11B are illustrated as being arranged to project laterally at rear surface 10B of main unit 10, but may be arranged to project longitudinally or diagonally. The position in which first plug 11A and second plug 11B are arranged is not limited to the above-described position unless display unit 40 is so inclined that it is difficult for the subject to look at the display when main unit 10 is mounted on the mounting surface.

Although the configuration is illustrated in which both the surfaces of region 11C of first tube 24A bulging outwardly and region 11D of second tube 24B bulging outwardly come into contact with the mounting surface, a configuration in which only one of the tubes comes into contact with the mounting surface may be adopted.

Second Embodiment

Figure 9:
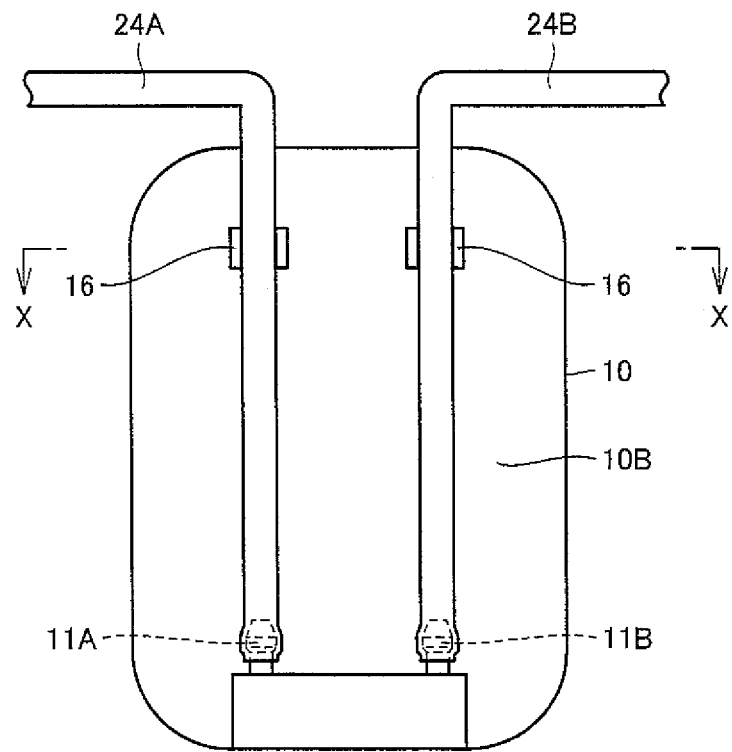
FIG. 9 shows a back side (rear surface) of a main unit of a blood pressure monitor according to a second embodiment with tubes connected thereto.
Figure 10:
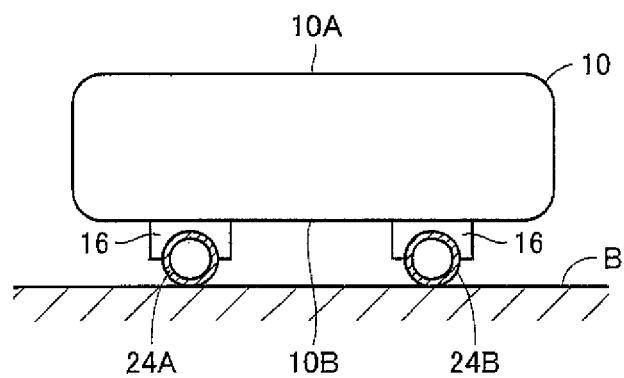
FIG. 10 is a sectional view taken along the line X-X in FIG. 9.

With reference to FIGS. 9 and 10, a manual blood pressure monitor according to a second embodiment will now be described. In the manual blood pressure monitor according to the present embodiment, a portion of each of first tube 24A and second tube 24B is arranged to extend longitudinally at the rear surface of main unit 10. The remaining configuration and hardware configuration are identical to those of the above-described first embodiment.

First plug 11A and second plug 11B are located in a lower region at the rear surface of main unit 10 to extend toward the upper region. First tube 24A fitted fixedly over first plug 11A and second tube 24B fitted fixedly over second plug 11B are led to extend toward the upper region of rear surface 10B of main unit 10, and supported fixedly by clips 16 provided at rear surface 10B of main unit 10.

In this manner, by leading first tube 24A and second tube 24B to extend toward the upper region of rear surface 10B of main unit 10, portions of first tube 24A and second tube 24B (portions located at rear surface 10B) support main unit 10 by the upper side of first tube 24A and second tube 24B, while coming into contact with the mounting surface by the lower side of first tube 24A and second tube 24B, as shown in FIG. 10.

Main unit 10 is therefore less likely to slide over mounting surface B even when main unit 10 is pulled by first tube 24A and second tube 24B. As a result, undesirable vibrations are not imparted to pressure sensor 32 and the like built into main unit 10, which can achieve improved accuracy in blood pressure measurement. In addition, the unnecessity to provide another member for preventing main unit 10 from sliding avoids an increase in the manufacturing cost of the manual pressurizing blood pressure monitor.

Although the above-described embodiments illustrate the configuration in which first plug 11A and second plug 11B are located in the lower region of the rear surface of main unit 10, and first tube 24A and second tube 24B are led toward the upper region of the rear surface of main unit 10, this configuration is not a limitative example. For example, a configuration may be adopted in which first plug 11A and second plug 11B are located in the upper region of the rear surface of main unit 10, and first tube 24A and second tube 24B are led toward the lower region of the rear surface of main unit 10.

Alternatively, first plug 11A and second plug 11B may be located in the central region of the rear surface of main unit 10, one of the tubes being led toward the upper region of the rear surface of main unit 10, while the other tube being led toward the lower region.

Although the above-described embodiments illustrate the case of arranging first plug 11A and second plug 11B at rear surface 10B of main unit 10, this configuration is not a limitative example. A configuration may be adopted in which one or both of first plug 11A and second plug 11B are arranged at a side surface of main unit 10, and first tube 24A and second tube 24B are arranged fixedly at the rear surface of main unit 10.

Although the configuration is illustrated in which first tube 24A and second tube 24B led from the plugs both come into contact with mounting surface B, a configuration in which only one of the tubes comes into contact with mounting surface B may be adopted.

In the above-described embodiments, first tube 24A and second tube 24B preferably have a thickness larger than or equal to about 0.5 mm in order to prevent rupture of the tubes caused by friction.

Figure 11:
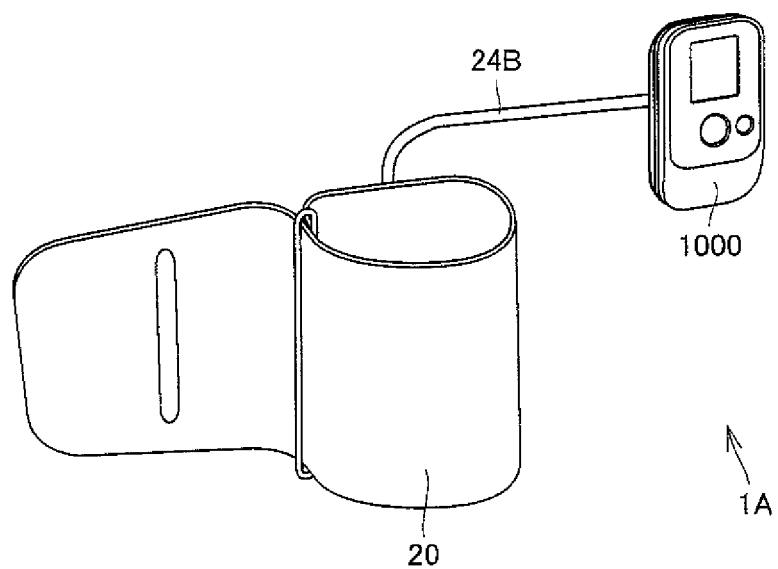
FIG. 11 shows an overall configuration of a blood pressure monitor according to another embodiment.

Although the blood pressure monitors according to the above-described embodiments are implemented by applying one or more embodiments of the present invention to manual pressurizing blood pressure monitors, one or more embodiments of the present invention may also be applied to an automatic pressurizing blood pressure monitor, as shown in FIG. 11. In an automatic pressurizing blood pressure monitor 1A, a main unit 1000 includes a pressurizing mechanism such as a small air pump or the like. Therefore, only tube 24B connected to cuff 20 is led from main unit 1000. By appropriately applying the above-described configurations shown in FIGS. 1 to 10 between main unit 1000 and tube 24B, main unit 1000 is less likely to slide over the mounting surface even when the main unit is pulled by tube 24B connected to main unit 1000.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A blood pressure monitor comprising:
a main unit configured to be mounted on a mounting surface and comprising a front surface and a rear surface;
a manual pressurizing mechanism;
a cuff configured to be wound around a subject's predetermined body section;
a first tube connecting said main unit and said manual pressurizing mechanism; and a second tube connecting said main unit and said cuff,
wherein at least one of said first tube and said second tube comprises a bulging region boated at the rear surface of said main unit that is configured to come into direct contact with said mounting surface to prevent the main unit from sliding over the mounting surface.

2. The blood pressure monitor according to claim 1,
wherein a first plug over which said first tube is fitted fixedly and a second plug over which said second tube is fitted fixedly are provided at said rear surface of said main unit, and wherein said first plug and said second plug are arranged at said rear surface of said main unit such that a first bulging region is formed by fitting said first tube over said first plug and a second bulging region is formed by fitting said second tube over said second plug.

3. The blood pressure monitor according to claim 1,
wherein a first plug over which said first tube is fitted fixedly and a second plug over which said second tube is fitted fixedly are provided at said rear surface of said main unit, and wherein said first tube and said second tube are fixed at said rear surface of said main unit such that a portion of said first tube fitted over said first plug to extend from said first plug and a portion of said second tube fitted over said second plug to extend from said second plug come into contact with said mounting surface.

4. The blood pressure monitor according to claim 1,
wherein said first tube and said second tube have a thickness larger than or equal to about 0.5 mm.

5. A blood pressure monitor comprising:
a main unit configured to be mounted on a mounting surface and comprising a front surface and a rear surface;
a cuff configured to be wound around a subject's predetermined body section; and
a tube connecting said main unit and said cuff,
wherein said tube comprises a bulging region located at the rear surface of said main unit that is configured to come into direct contact with said mounting surface to prevent the main unit from sliding over the mounting surface.

\* \* \* \* \*